United States Patent [19]

Seibert

[11] Patent Number: 4,479,887

[45] Date of Patent: Oct. 30, 1984

[54] POLYETHER DERIVATIVES, THEIR USE AS EMULSIFIERS, AND EMULSIONS CONTAINING THE NEW POLYETHER DERIVATIVE

[75] Inventor: Karl Seibert, Dueren-Niederau, Fed. Rep. of Germany

[73] Assignee: Akzona Incorporated, Asheville, N.C.

[21] Appl. No.: 470,900

[22] Filed: Feb. 28, 1983

[30] Foreign Application Priority Data

Mar. 3, 1982 [DE] Fed. Rep. of Germany ....... 3207612

[51] Int. Cl.$^3$ ...................... B01J 13/00; B01F 17/42
[52] U.S. Cl. .................................. 252/309; 252/312; 252/351; 252/DIG. 1; 424/170
[58] Field of Search .................. 252/309, 312, 351

[56] References Cited

U.S. PATENT DOCUMENTS 4,207,421  6/1980  Scardera et al. .................. 252/351
4,252,540  2/1981  Yamamwa et al. ............... 252/351
4,302,349 11/1981  Kosswig et al. ................... 252/351

*Primary Examiner*—Richard D. Lovering
*Assistant Examiner*—Anne Brookes
*Attorney, Agent, or Firm*—Francis W. Young; Jack H. Hall

[57] ABSTRACT

New polyether derivatives obtained by gradually adding at temperatures between 100° and 200° C. a long-chain 1,2-epoxide having a chain length of 10 to 32 carbon atoms to either (1) polyethylene glycol monoalkyl ether whose mean molecular weight is 400 to 2500 and whose alkyl group contains 1 to 3 carbon atoms; or to (2) a polyethylene glycol-polypropylene glycol monoalkyl ether whose mean molecular weight is 450 to 3100, whose recurring ethylene oxide units and propylene oxide units form a block each, the polypropylene glycol block having a mean molecular weight of not more than 600 and whose alkyl group forms the end of the polyethylene glycol block and contains 1 to 3 carbon atoms, using 0.1 to 1% by weight of alkali hydroxide related to the total amount of the starting substances.

These polyether derivatives correspond to the general formula:

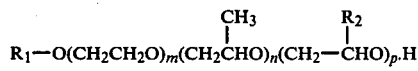

wherein
  $R_1$ represents an aliphatic hydrocarbon radical containing 1 to 3 carbon atoms;
  $R_2$ represents an aliphatic hydrocarbon radical containing 8 to 30 carbon atoms;
  $m = 10-50$ (mean value);
  $n = 0-10$ (mean value);
  $p = 1-10$ (mean value).

The derivatives are suitable emulsifiers in emulsions, particularly in water-in-oil emulsions.

16 Claims, No Drawings

POLYETHER DERIVATIVES, THEIR USE AS EMULSIFIERS, AND EMULSIONS CONTAINING THE NEW POLYETHER DERIVATIVE

SUMMARY OF THE INVENTION

The present invention is directed to new polyether derivatives prepared by the gradual addition of a long-chain 1,2-epoxy with a chain length of 10 to 32 carbon atoms, at temperatures from 100° to 200° C., to an alcohol ethoxylate, specifically, either (1) polyethylene glycol monoalkylether, the average molecular weight of which is 400 to 2500 and the alkyl group of which contains 1 to 3 carbon atoms; or to (2) a polyethylene glycol-polypropylene glycol monoalkylether, the average molecular weight of which is 450 to 3100 and the repeating ethylene oxide and propylene oxide units of which form one block each, with the polypropylene glycol block having an average molecular weight of at most 600, whereby its alkyl group forms the end of the polyethylene glycol block and contains 1 to 3 carbon atoms, making use of 0.1 to 1% by weight of alkali hydroxide, referred to the total quantity of the initial materials. In this specification, the initial materials are the 1-2-epoxy and the alcohol ethoxylate.

These polyether derivatives correspond to the general formula:

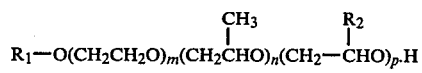

$$R_1-O(CH_2CH_2O)_m(CH_2\overset{CH_3}{\underset{|}{C}}HO)_n(CH_2-\overset{R_2}{\underset{|}{C}}HO)_p \cdot H$$

wherein
- $R_1$ = an aliphatic hydrocarbon radical containing 1 to 3 carbon atoms;
- $R_2$ = an aliphatic hydrocarbon radical containing 8 to 30 carbon atoms;
- m = 10–50 (average);
- n = 0–10 (average);
- p = 1–10 (average).

In this specification, the terms "mean value" and "average" are used interchangeably. The new polyether derivatives are prepared in a manner analogous to the known reactions of alcohols with 1,2-epoxides, as described in Houben-Weyl, *Methoden der organischen Chemie* (Methods of Organic Chemistry), vol. 14.2, pp. 436–450 (1965).

DESCRIPTION OF THE PREFERRED EMBODIMENTS

Known emulsifiers include sorbitan, fatty acid esters and their ethoxylates, nonionogenic anion-active and cation-active detergents, partial ester salts of phosphoric acid, and the like. Ester compounds preponderate among known emulsifiers, but they have the disadvantage of being very hydrolysis-sensitive. Emulsifiers containing amine nitrogen in bound form are generally toxic and irritating to the skin. The polyether derivatives pursuant to the invention are especially well suited for emulsifiers and, in contrast to most of the known emulsifiers, can be used in oil-in-water as well as in water-in-oil emulsions. Thus, the present derivatives are excellently suited for cosmetic and industrial emulsions. Compared to esters, they are singularly resistant to hydrolyzation. Antioxidants are not required. They are dermatologically and toxicologically unobjectionable.

Preferred polyether derivatives are those in which the chain length of the long-chain epoxy is 12 to 20 carbon atoms ($R_2$=10–18). Also preferred are polyether derivatives in which the alkyl radical is a methyl group.

Pursuant to the invention, the new polyether derivatives are used as emulsifiers. Depending upon the structure of the molecule, the derivatives can be used as effective emulsifiers in either oil-in-water emulsions or water-in-oil emulsions. The derivatives are suitable emulsifiers for oil-in-water emulsions when the proportion of polyether blocks comprised of polyethylene oxide units and, if required, of polypropylene oxide units, is at least 60% by weight of the total polyether derivative. Excellent emulsifiers for water-in-oil emulsions are those in which the proportion of polyether blocks made up of polyethylene oxide units and, if required, of polypropylene oxide units, amount to no more than 50% of the total polyether derivative. For cosmetic applications, the water-in-oil emulsions are preferred. Specifically, the present emulsifiers have a spontaneous emulsifying effect on cosmetics, and result in creams having a smooth and bright appearance and which are not sticky and are easily distributed on the skin.

The emulsifiers pursuant to the invention are colorless, odorless, and resistant to oxidative influences. The emulsions prepared in this manner can be used without difficulty by persons with a sensitive skin, and leave a pleasant feeling thereon. Only minimal amounts of perfumes need be added, as the emulsifier has no unpleasant odor to mask. This factor is also beneficial for persons with a sensitive skin.

The emulsions pursuant to the invention are prepared in a simple manner, i.e., by dissolving the polyether derivatives used as emulsifiers in the oil phase at a temperature of about 75° C., followed by the slow addition of the water phase heated to about 75° C., with stirring of the resulting emulsion. It is most expedient to dissolve or distribute materials to be contained in, for example, the cosmetic emulsions, such as skin moisture regulators, plant extracts of active substances, vitamins, hormones, pigments, salts, perfume oils, UV filtering agents, or dyestuffs, in the phase which will best accept them. The required quantity of emulsifier is 0.5 to 10% by weight, referred to the total weight of the emulsion. The quantity of water to be incorporated may amount to 20 to 80% by weight, referred to the total weight of the emulsion.

Customarily utilized products, such as animal and vegetable oils and fats; synthetic esters of fatty acids with aliphatic alcohols; higher fatty alcohols; waxes; the so-called mineral fats and oils, such as paraffin oil, vaseline or ceresin; silicone oils; and silicone fats can be considered as the oil phase of the emulsion pursuant to the invention. The following examples are intended to explain the invention in greater detail.

EXAMPLE 1

The appropriate alcohol ethoxylate is melted in a three-necked flask having a stirrer, descending condenser, thermometer and gas supply tube, under a nitrogen atmosphere and mixed with 0.5% (wt.) of a 45% aqueous potassium hydroxide solution. The substance is heated to 60° C. in 0.5 hours by passing nitrogen through it. A water-jet vacuum is then applied, and the substance is heated to 100° C. over the next 0.5 hours and held at this temperature under the vacuum for 0.5 hours. The vacuum is released by adding nitrogen, and the substance heated to 180° C. in 0.5 hours. The epoxyalkane is added dropwise over the next one hour. The reaction has come to an end after an additional reaction time of 2 hours, and each of the present compounds prepared in this manner is then cooled to 100° C. and neutralized with 90% lactic acid.

The composition and characteristics of products prepared in this manner are compiled in Table 1. For each of these products, the following alcohol ethoxylated and epoxyalkanes were used:

| Product | Alcohol Ethoxylates | Epoxyalkane |
|---|---|---|
| A | $CH_3$—O—$(CH_2CH_2O)_{22.39}$—H | $(CH_2$—$CH(C_{10}H_{21}))$—O) |
| B | $CH_3$—O—$(CH_2CH_2O)_{16.7}$—H | $(CH_2$—$CH(C_{10}H_{21}))$—O) |
| C | $CH_3$—O—$(CH_2CH_2O)_{22.39}$—H | $(CH_2$—$CH(C_{16}H_{33}))$—O) |
| D | $C_3H_7$—O—$(CH_2CH_2O)_{22.39}$—$(CH_2CH(CH_3)$—O$)_2$—H | $(CH_2$—$CH(C_{10}H_{21}))$—O) |

TABLE 1

| PRODUCT | $R_1$ | m | n | p | $R_2$ | AVERAGE MOLECULAR WEIGHT | SOLIDIFICATION POINT | DENSITY | APPEARANCE |
|---|---|---|---|---|---|---|---|---|---|
| A | $CH_3$ | 22.39 | 0 | 7.35 | $C_{10}H_{21}$ | 1,750 | — | 0.9454 g/cc at 50° C. | yellowish viscous liquid |
| B | $CH_3$ | 16.7 | 0 | 1.18 | $C_{10}H_{21}$ | 1,050 | 29–32.0° C. | 1.0220 g/cc at 50° C. | light paste |
| C | $CH_3$ | 22.39 | 0 | 1.43 | $C_{16}H_{33}$ | 1,350 | 38.5–40.5° C. | 0.9850 g/cc at 70° C. | white wax |
| D | $C_3H_7$ | 22.39 | 2 | 7.35 | $C_{10}H_{21}$ | 1,850 | — | 0.967 g/cc at 50° C. | yellowish viscous liquid |

Products A and D are water-in-oil emulsifiers, whereas products B and C are oil-in-water emulsifiers.

EXAMPLE 2

Preparation of the Emulsions

The water-in-oil and oil-in-water emulsions referred to in the following examples were prepared by heating the present emulsifiers together with the other components of the fatty phase to 75° C. Separately, the components of the water phase were likewise heated to 75° C. and then slowly added to the hot fatty phase with initially rapid stirring. If desired, perfume may be added after the finished emulsion has cooled. The emulsions in which commercially available emulsifiers had been used for comparison purposes were prepared in a corresponding manner. The stability in storage of all the resulting emulsions was evaluated by checking them during a period of at least 3 months for oil or water separation. Their thermal stability was determined at 45° C. as was their resistance to cold at temperatures of −5° C.; their stability at 20° C. was determined as well. The storage stability was evaluated by means of the following grades:
 1 = very good
 2 = usable
 3 = useless

EXAMPLE 3

Water-in-oil Emulsion

Fatty phase
 3.0 parts emulsifier
 3.0 parts lanolin
 5.0 parts lanolin alcohol
 3.0 parts triglyceride of hydroxystearic acid
 14.0 parts paraffin oil
 0.2 parts preservative Water phase
 5.0 parts sorbitol 70%
 0.5 parts magnesium sulfate
 0.2 parts borax
 65.6 parts water
 0.5 parts perfume oil The emulsions were prepared by using emulsifiers
 E I = emulsifier A
 E II = emulsifier D
 E III = sorbitan monooleate

| CHARACTERISTICS | E I | E II | E III |
|---|---|---|---|
| Storage stability | 1 | 1 | 2 |
| Heat stability | 1 | 1 | 3 |
| Cold stability | 1 | 2 | 3 |

EXAMPLE 4

Fatty phase
 3.0 parts emulsifier
 3.0 parts PEG 20/dodecyl glycol copolymer
 5.0 parts microwax
 17.0 parts paraffin oil
 2.0 parts lanolin alcohol Water phase
 5.0 parts sorbitol 70%
 65.0 parts water The following emulsifiers were used:
 E III = emulsifier A
 E IV = polyglycerin isostearate
 E V = decaglycerol decaoleate
 E VI = mixture of oleylphosphoric esters

| CHARACTERISTICS | E III | E IV | E V | E VI |
|---|---|---|---|---|
| Storage stability | 1 | 1 | 1 | 1 |
| Heat stability | 1 | 2 | 2 | 2 |
| Cold stability | 1 | 2 | 2 | 2 |

EXAMPLE 5

Fatty phase
 3.0 parts emulsifier
 5.0 parts absorption base
 5.0 parts beeswax
 20.0 parts isopropyl stearate Water phase
 5.0 parts sorbitol 70%
 62.0 parts water The following emulsifiers were used:
 E VII = emulsifier A
 E VIII = polyglycerin isostearate

| CHARACTERISTICS | E VII | E VIII |
|---|---|---|
| Storage stability | 1 | 1 |
| Heat stability | 1 | 1 |
| Cold stability | 1 | 2 |

EXAMPLE 6

Fatty phase
  2.0 parts emulsifier
  5.0 parts isocetyl stearate
  5.0 parts glycerin monostearate 90%
  6.0 parts stearic acid
  0.2 parts preservative
Water phase
  3.0 parts glycerin
  0.3 parts preservative
  77.2 parts water
  0.3 parts perfume oil
The following emulsifiers were used:
  E IX = emulsifier B
  E X = emulsifier C
  E XI = polyoxyethylene glycerinmonooleate

| CHARACTERISTICS | E IX | E X | E XI |
|---|---|---|---|
| Storage stability | 1 | 1 | 1 |
| Heat stability | 1 | 3 | 3 |
| Cold stability | 1 | 3 | 3 |

EXAMPLE 7

Fatty phase
  3.0 parts emulsifier
  2.0 parts acetylated lanolin
  1.6 parts glycerin monostearate
  2.0 parts stearic acid
  6.0 parts paraffin oil
  2.0 parts cetyl alcohol
  0.2 parts preservative
Water phase
  5.0 parts sorbitol 70%
  1.5 parts magnesium aluminum silicate
  0.3 parts preservative
  76.2 parts water
  0.2 parts perfume oil
The following emulsifiers were used:
  E XII = emulsifier B
  E XIII = emulsifier C
  E XIV = polyoxyethylene methylglucoside sesquistearate ester

| CHARACTERISTICS | E XII | E XIII | E XIV |
|---|---|---|---|
| Storage stability | 1 | 1 | 3 |
| Heat stability | 1 | 1 | 3 |
| Cold stability | 1 | 2 | 3 |

EXAMPLE 8

Oil-in-water Emulsion

Fatty phase
  3.0 parts emulsifier
  6.0 parts montan wax
  9.0 parts isopropyl stearate
  2.0 parts sesame oil
  0.02 parts antioxidants
  0.2 parts preservative
Water phase
  0.3 parts triethanolamine
  0.3 parts carboxyvinyl polymer
  0.3 parts preservative
  78.68 parts water
  0.2 parts perfume oil
The following emulsifiers were used:
  E XV = emulsifier B
  E XVI = emulsifier C
  E XVII = a mixture of fatty alcohol tetraglycolphosphoric esters

| CHARACTERISTICS | E XV | E XVI | E XVII |
|---|---|---|---|
| Storage stability | 1 | 1 | 1 |
| Heat stability | 1 | 1 | 3 |
| Cold stability | 1 | 1 | 2 |

I claim:

1. A polyether derivative prepared by gradual addition of a long-chain aliphatic 1,2-epoxy with a chain length of 10 to 32 carbon atoms, at temperatures from 100° to 200° C., to an alcohol ethoxylate, in the presence of 0.1 to 1% by weight of alkali hydroxide, based on the total quantity of said 1,2-epoxy and said alcohol ethoxylate, said alcohol ethoxylate being either (1) a polyethylene glycol monoalkylether, the average molecular weight of which amounts to 400 to 2500 and the alkyl group of which contains 1 to 3 carbon atoms; or (2) a polyethylene glycol-polypropylene glycol monoalkylether with an average molecular weight of 450 to 3100, the repeating ethylene oxide and propylene oxide units of which form one block each, whereby the polypropylene glycol block has an average molecular weight of at most 600 and the alkylether group of which forms the end of the polyethylene glycol block and contains 1 to 3 carbon atoms.

2. The polyether derivative as set forth in claim 1, characterized in that the chain length of the long-chain epoxy is on the average of from 12 to 20 carbon atoms.

3. The polyether derivative as set forth in claim 1, wherein the alkyl group is a methyl group.

4. The polyether derivative as set forth in claim 2, wherein the alkyl group is a methyl group.

5. An oil-in-water or water-in-oil emulsion, wherein said emulsion is emulsified by an emulsifier, said emulsifier being a polyether derivative prepared by gradual addition of a long-chain aliphatic 1,2-epoxy with a chain length of 10 to 32 carbon atoms, at temperatures from 100° to 200° C. in the presence of 0.1 to 1% by weight of alkali hydroxide, based on the total quantity of the initial materials, to either (1) a polyethylene glycol monoalkylether, the average molecular weight of which amounts to 400 to 2500 and the alkyl group of which contains 1 to 3 carbon atoms; or to (2) a polyethylene glycol-polypropylene glycol monoalkylether with an average molecular weight of 450 to 3100, the repeating ethylene oxide and propylene oxide units of which form one block each, whereby the polypropylene glycol block has an average molecular weight of at most 600 and the alkylether group of which forms the end of the polyethylene glycol block and contains 1 to 3 carbon atoms.

6. The emulsion as set forth in claim 5, wherein the chain length of said long-chain epoxy is on the average 12 to 20 carbon atoms.

7. The emulsion as set forth in claim 5, wherein the alkyl group is a methyl group.

8. The emulsion as set forth in claim 6, wherein the alkyl group is a methyl group.

9. A water-in-oil emulsion, wherein said emulsion is emulsified by an emulsifier, said emulsifier being a polyether derivative prepared by gradual addition of a long-chain aliphatic 1,2-epoxy with a chain length of 10 to 32 carbon atoms, at temperatures from 100° to 200° C. in the presence of 0.1 to 1% by weight of alkali hydroxide, based on the total quantity of the initial materials, to either (1) a polyethylene glycol monoalkylether, the average molecular weight of which amounts to 400 to 2500 and the alkyl group of which contains 1 to 3 carbon atoms; or to (2) a polyethylene glycol-polypropylene glycol monoalkylether with an average molecular weight of 450 to 3100, the repeating ethylene oxide and propylene oxide units of which form one block each, whereby the polypropylene glycol has an verage molecular weight of at most 600 and the alkylether group of which forms the end of the polyethylene glycol block and contains 1 to 3 carbon atoms.

10. The emulsion as set forth in claim 9, wherein the chain length of said long-chain epoxy is on the average 12 to 20 carbon atoms.

11. The emulsion as set forth in claim 9, wherein the alkyl group is a methyl group.

12. The emulsion as set forth in claim 10, wherein the alkyl group is a methyl group.

13. An oil-in-water or water-in-oil emulsion, wherein said emulsion is emulsified by 0.5% to 10% (weight) of an emulsifier, said emulsifier being a polyether derivative prepared by gradual addition of a long-chain aliphatic 1,2-epoxy with a chain length of 10 to 32 carbon atoms, at temperatures from 100° to 200° C., to either (1) a polyethylene glycol monoalkylether, the average molecular weight of which amounts to 400 to 2500 and the alkyl group of which contains 1 to 3 carbon atoms; or to (2) a polyethylene glycol-polypropylene glycol monoalkylether with an average molecular weight of 450 to 3100, the repeating ethylene oxide and propylene oxide units of which form one block each, whereby the polypropylene glycol block has an average molecular weight of at most 600 and the alkylether group of which forms the end of the polyethylene glycol block and contains 1 to 3 carbon atoms, utilizing 0.1 to 1% by weight of alkali hydroxide, referred to the total quantity of the initial materials.

14. The emulsion as set forth in claim 13, wherein the chain length of said long-chain epoxy is on the average 12 to 20 carbon atoms.

15. The emulsion as set forth in claim 13, wherein the alkyl group is a methyl group.

16. The emulsion as set forth in claim 14, wherein the alkyl group is a methyl group.

* * * * *